United States Patent
Kurihara et al.

(10) Patent No.: US 10,765,568 B2
(45) Date of Patent: Sep. 8, 2020

(54) ABSORBENT ARTICLE

(71) Applicant: DAIO PAPER CORPORATION, Ehime (JP)

(72) Inventors: Ryoko Kurihara, Tochigi (JP); Mariko Nagashima, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 295 days.

(21) Appl. No.: 15/778,471

(22) PCT Filed: Nov. 30, 2016

(86) PCT No.: PCT/JP2016/085498
§ 371 (c)(1),
(2) Date: May 23, 2018

(87) PCT Pub. No.: WO2017/094755
PCT Pub. Date: Jun. 8, 2017

(65) Prior Publication Data
US 2018/0344537 A1 Dec. 6, 2018

(30) Foreign Application Priority Data

Nov. 30, 2015 (JP) .................. 2015-234218

(51) Int. Cl.
*A61F 13/512* (2006.01)
*A61F 13/511* (2006.01)
(Continued)

(52) U.S. Cl.
CPC .... *A61F 13/5126* (2013.01); *A61F 13/15203* (2013.01); *A61F 13/511* (2013.01);
(Continued)

(58) Field of Classification Search
CPC .............. A61F 13/511; A61F 13/51104; A61F 13/51108; A61F 13/51113;
(Continued)

(56) References Cited

U.S. PATENT DOCUMENTS

2,902,037 A * 9/1959 Harwood .............. A61F 13/511
604/365
3,110,609 A * 11/1963 Bletzinger ............... D04H 5/04
428/195.1
(Continued)

*Primary Examiner* — Catharine L Anderson
(74) *Attorney, Agent, or Firm* — Wenderoth, Lind & Ponack, L.L.P.

(57) ABSTRACT

There is provided an absorbent article with its front-surface sheet composed of cotton fibers by which liquid reversion is prevented and water retention on the front-surface sheet is minimized. An incontinence pad 1 is provided that is configured to absorb urine at medium or more volume that is 20 cc or more. A front-surface sheet 3 is formed of a spunlace nonwoven fabric 100 wt % of which is composed of cotton fibers and which is coated with a water repellent agent, and has, at least at a portion corresponding to an excreting hole, numerous front-face/back-face penetrating openings 10 that are longer shaped in the longitudinal direction of the incontinence pad 1. The cotton fibers form numerous longitudinal streaks 11 and numerous lateral streaks 12, the longitudinal streaks extending along the longitudinal direction of the incontinence pad 1 and being formed with an interval in the width direction of the incontinence pad 1, and the lateral streaks extending along the width direction of the incontinence pad 1 and connecting together the longitudinal streaks formed with an interval in the longitudinal direction of the incontinence pad 1. The openings 10 are formed within portions surrounded by the longitudinal streaks 11 and the lateral streaks 12. The longitudinal streaks 11 have more fibers and are formed at a higher density than the lateral streaks 12.

8 Claims, 4 Drawing Sheets

(51) Int. Cl.
*A61F 13/15* (2006.01)
*A61F 13/515* (2006.01)
*A61L 15/20* (2006.01)
*A61L 15/60* (2006.01)
*A61F 13/51* (2006.01)

(52) U.S. Cl.
CPC .......... *A61F 13/512* (2013.01); *A61F 13/515* (2013.01); *A61L 15/20* (2013.01); *A61L 15/60* (2013.01); *A61F 2013/1556* (2013.01); *A61F 2013/15406* (2013.01); *A61F 2013/5104* (2013.01); *A61F 2013/51021* (2013.01); *A61F 2013/51147* (2013.01)

(58) Field of Classification Search
CPC .............. A61F 13/51121; A61F 13/512; A61F 13/5122; A61F 13/5126; A61F 2013/51117; A61F 2013/51139; A61F 2013/51152; A61F 2013/5127; A61F 2013/5128; A61F 2013/530386; A61F 2013/53043
See application file for complete search history.

(56) References Cited

U.S. PATENT DOCUMENTS

| | | | | |
|---|---|---|---|---|
| 4,741,941 A | * | 5/1988 | Englebert | A47L 13/16 15/209.1 |
| 6,106,925 A | * | 8/2000 | Palumbo | A61F 13/512 428/137 |
| 7,897,240 B2 | * | 3/2011 | Noda | A61F 13/51 428/113 |

* cited by examiner

ABSORBENT ARTICLE

TECHNICAL FIELD

The present invention relates to absorbent articles mainly for use in incontinence pads, and in particular, relates to incontinence pads for use in absorbing urine at medium or more volume that is 20 cc or more in total.

BACKGROUND ART

Absorbent articles including incontinence pads and those for females including discharge sheets, pantyliners and sanitary napkins are conventionally known to be formed from a liquid-impermeable back-surface sheet, such as a polyethylene sheet or a polyethylene sheet-laminated nonwoven fabric; a front-surface sheet; and an absorber that is composed of a cellulose wadding, e.g., crushed pulp, and that is interposed between the back-surface sheet and the front-surface sheet.

The front-surface sheet, due to forming a skin-contacting face, is demanded to be soft, provide a texture felt to be dry even after absorbing excreted liquid, less stimulate the skin and such. Materials that meet such demands and widely employed in the field of absorbent articles, particularly in the field of incontinence pads, are nonwoven fabrics formed of synthetic fibers or mesh sheets composed of resins. Nonetheless, the front-surface sheet composed of synthetic fibers can be a cause of problems such as itch and rash.

A proposal made for addressing the above issue is a front-surface sheet formed of cotton fibers (cotton). With absorbent articles demanded to include a front-surface sheet having a high liquid-permeability and being quick to allow liquid to reach an absorber, the inclusion of usual defatted cotton fibers in the front-surface sheet involves problems: the exhibition of high water retainability by the front-surface sheet itself, with a result that the sense of stickiness is likely to remain on the front-surface.

Such an absorbent article with its front-surface sheet composed of cotton fibers, though beneficially realizing the texture felt to be as soft as underwear, has a high liquid retainability as described above. For this reason, body fluid when excreted in a large amount, by remaining on such a front-surface sheet, would cause stuffiness, rash and other problems in long-hour wearing of such an absorbent article. Thus, use of conventional absorbent articles with their front-surface sheet composed of cotton fibers have been limited to such products as discharge sheets, which do not need to absorb much amount of body fluid.

An example of such an absorbent article with its front-surface sheet composed of cotton fibers is the one disclosed in Patent Literature 1. Patent Literature 1 discloses an absorbent article with its top sheet composed of spunlace nonwoven fabrics that are composed of 40 to 100 wt % of cotton fibers and 60 to 0 wt % of synthetic fibers and are coated with a water repellent agent, wherein the top sheet has, on its skin-contacting face, a water absorbing capacity of 0 mm to 5 mm, and has, at least at its portion corresponding to an excreting hole, numerous front-face/back-face penetrating openings. Such an absorbent article having the top sheet that is composed of spunlace nonwoven fabrics composed of a high content of cotton fibers provides some benefits inherent in the cotton fibers, such as the texture felt good to the skin and the unlikeliness to cause such problems as itch and rash; and another benefit is that the problem of the liquid remaining on the front-surface is adequately addressed by the water repellent agent applied (externally-added) thereby ensuring that the skin-contacting face has a sufficiently low water absorbing capacity. In response to the problem that merely lowering the water absorbing capacity does not enable liquid of an excreted substance to easily pass through the top sheet, which would possibly cause e.g., sideward liquid leakage, the top sheet of the absorbent article described in Patent Literature 1 has, at least at its portion corresponding to an excreting hole, the numerous front-face/back-face penetrating openings aimed at prompt liquid absorption. This configuration is described in Patent Literature 1 as bringing about benefits such as adequate prevention of stickiness that would be caused by the liquid remaining on the front-surface, and the inhibition of the excreted liquid that has been absorbed from reverting to the front-face of the top sheet due to the water repellency exhibited by the top sheet.

CITATION LIST

Patent Literature

Patent Literature 1: JP-A-2010-269029

SUMMARY OF INVENTION

Technical Problem

However, in absorbing urine at medium or more volume that is 20 cc or more in total, the absorbent article described in Patent Literature 1 has a potential of letting water be retained on the front-surface sheet, and therefore would need some contrivance for minimizing the water retention on the front-surface sheet.

In addition, in view of the configuration that absorbent articles are formed with a shape long and narrow in their longitudinal direction, the promotion of the urine diffusion in the longitudinal direction of the absorbent articles has been demanded for the prevention of sideward urine leakage.

A primary object to be attained by the present invention is therefore to provide an absorbent article with its front-surface sheet composed of cotton fibers wherein the front-surface sheet has a minimized water retention and permits an easy liquid diffusion in the longitudinal direction of the absorbent article.

Solution to Problem

To attain the above-mentioned object, the present invention according to claim 1 provides an absorbent article comprising a front-surface sheet, a back-surface sheet, and an absorber interposed between the front-surface sheet and the back-surface sheet, wherein:

the absorbent article is an incontinence pad for use in absorbing urine at a medium or more volume that is 20 cc or more;

the front-surface sheet is formed of a spunlace nonwoven fabric 100 wt % of which is composed of cotton fibers and which is coated with a water repellent agent and has, at least at a portion corresponding to an excreting hole, numerous front-face/back-face penetrating openings that are longer shaped in the longitudinal direction of the absorbent article;

the cotton fibers form numerous longitudinal streaks and numerous lateral streaks, the longitudinal streaks extending along the longitudinal direction of the absorbent article and being formed with an interval in the width direction of the absorbent article, and the lateral streaks extending along the width direction of the absorbent article and connecting together the longitudinal streaks formed with an interval in the longitudinal direction of the absorbent article; the openings are formed within portions surrounded by the longitudinal streaks and the lateral streaks; and the longitudinal streaks have more fibers and are formed at a higher density than the lateral streaks.

The invention defined in the claim 1 is directed to an incontinence pad configured to absorb urine excreted instantaneously at the time of application of force with respect to abdomen, such as at the time of sneezing, coughing and carrying something heavy and configured to absorb urine at medium or more volume that is 20 cc or more in total. There are many cases where incontinence pads keep being worn until incontinence experienced for the second time: incontinence pads, through incontinence experienced for the first time, keep being worn for long hours till the second urination, after which the pads are disposed of.

In the absorbent article according to the present invention, the front-surface sheet is formed of a spunlace nonwoven fabric 100 wt % of which is composed of cotton fibers and which is coated with a water repellent agent, and has numerous front-face/back-face penetrating openings at least at its portion corresponding to an excreting hole. The spunlace nonwoven fabric with such a high content of cotton fibers provides a texture felt soft to the skin and realizes the unlikeliness to cause skin problems such as itch and rash that would be experienced in long-hour wearing of the absorbent article. The coating with the water repellent agent adequately addresses the problem of the liquid remaining on the front-surface. The configuration of the front-surface sheet having numerous front-face/back-face penetrating openings at least at its portion corresponding to an excreting hole allows for the prompt permeation of the body fluid.

In order to enable the front-surface sheet to have a minimized water retention and cause liquid to diffuse in the longitudinal direction of the absorbent article, the absorbent article according to the present invention has, at least at its portion corresponding to an excreting hole, the openings that are longer shaped in the longitudinal direction of the absorbent article. Compared with circular-shaped openings, the openings shaped in that way allow the liquid to pass therethrough more easily, with a result that through those openings, urine is able to pass through the front-surface sheet more easily, contributing to the front-surface sheet having a reduced water retention. In addition, those openings cause urine passing therethrough to deform so as to have a longitudinally-longer shape; this configuration makes it possible to control the direction of urine diffusion to accord with the longitudinal direction of the absorbent article thereby inhibiting transverse urine diffusion that would possibly cause sideward urine leakage.

In the absorbent article according to the present invention, the cotton fibers form numerous longitudinal streaks and numerous lateral streaks. The longitudinal streaks extend along the longitudinal direction of the absorbent article and are formed with an interval in the width direction of the absorbent article. The lateral streaks extend along the width direction of the absorbent article and connect together the longitudinal streaks formed with an interval in the longitudinal direction of the absorbent article. The openings are formed within portions surrounded by those longitudinal streaks and those lateral streaks. The longitudinal streaks have more fibers and are formed at a higher density than the lateral streaks. These configurations allow the longitudinal streaks alone to contact the skin, thereby reducing the skin contact area. Consequent benefits are the inhibited occurrence of skin problems, such as itch and rash, which would be experienced in long-hour wearing, and the alleviation of the sense of stickiness even after incontinence. Also, these configurations allow urine passing through the front-surface sheet to more easily diffuse, along the highly-dense longitudinal streaks, in the longitudinal direction of the absorbent article; and the diffusion direction of urine passing through the openings accords with the diffusion direction of urine permeating the front-surface sheet. As a result, urine is caused to permeate the front-surface sheet in such a manner as is drawn by the urine passing through the openings. Consequently, the liquid remaining on the front-surface sheet is minimized.

The present invention according to claim 2 provides the absorbent article according to claim 1, wherein the absorber is composed of synthetic fibers-free pulp fibers and superabsorbent polymers; the pulp fibers have a basis weight of 75 to 300 $g/m^2$, and the superabsorbent polymers have a basis weight of 85 to 185 $g/m^2$; and a ratio of the pulp fibers to the superabsorbent polymers is pulp fibers: superabsorbent polymers=70-30 wt %: 30-70 wt %.

The invention defined in the claim 2 employs the absorber which is composed of the pulp fibers and the superabsorbent polymers, each component at the specific basis weight, at the specific weight ratio of the pulp fibers to the superabsorbent polymers. By virtue of this configuration, urine excreted instantaneously is quickly absorbed, immediately after urination, by the pulp fibers, which have a higher absorption speed, and the urine absorbed by the pulp fibers is gradually absorbed and retained by the superabsorbent polymers, whereby urine is completely prevented from going back to the front-surface sheet. The incorporation of the pulp fibers at more than 70 wt % and the superabsorbent polymers at less than 30 wt %, which means a higher content of the pulp fibers, would reduce the liquid retainability of the absorber, which possibly leads to the urine going back to the front-surface sheet after urination. The incorporation of the pulp fibers at less than 30 wt % and the superabsorbent polymers at more than 70 wt %, which means a higher content of the superabsorbent polymers, would reduce the initial absorption speed immediately after urination, which possibly causes the liquid to remain on the front-surface sheet immediately after urination.

The present invention according to claim 3 provides the absorbent article according to claim 1 or 2, wherein the front-surface sheet is composed of non-defatted cotton fibers.

The invention defined in the claim 3 employs the front-surface sheet that is composed of non-defatted cotton fibers. Natural fat and oil of cotton wax adhering onto surfaces of the cotton fibers enables the front-surface sheet to be more unlikely to absorb the body fluid.

The present invention according to claim 4 provides the absorbent article according to any one of claims 1 to 3, wherein the water repellent agent comprises glyceryl stearate.

The invention defined in the claim 4 employs the water repellent agent that is glyceryl stearate. This configuration prevents urine from being absorbed by the cotton fibers of the front-surface sheet and instead makes urine flow to the absorber side more easily.

Advantageous Effects of Invention

As described in detail in the foregoing, the present invention makes it possible, in an absorbent article with its front-surface sheet composed of cotton fibers, for the front-surface sheet to have a minimized water retention.

DESCRIPTION OF EMBODIMENTS

Hereinafter, embodiments of the present invention will be described in detail with reference to drawings. The present invention provides an incontinence pad 1, suited for use in absorbing urine at medium or more volume that is 20 cc or more in total and especially suited for use in absorbing urine excreted instantaneously at the time of the application of force with respect to abdomen, such as at the time of sneezing, coughing and carrying something heavy.

<An Aspect of Basic Structure of Incontinence Pad>

Figure 1:
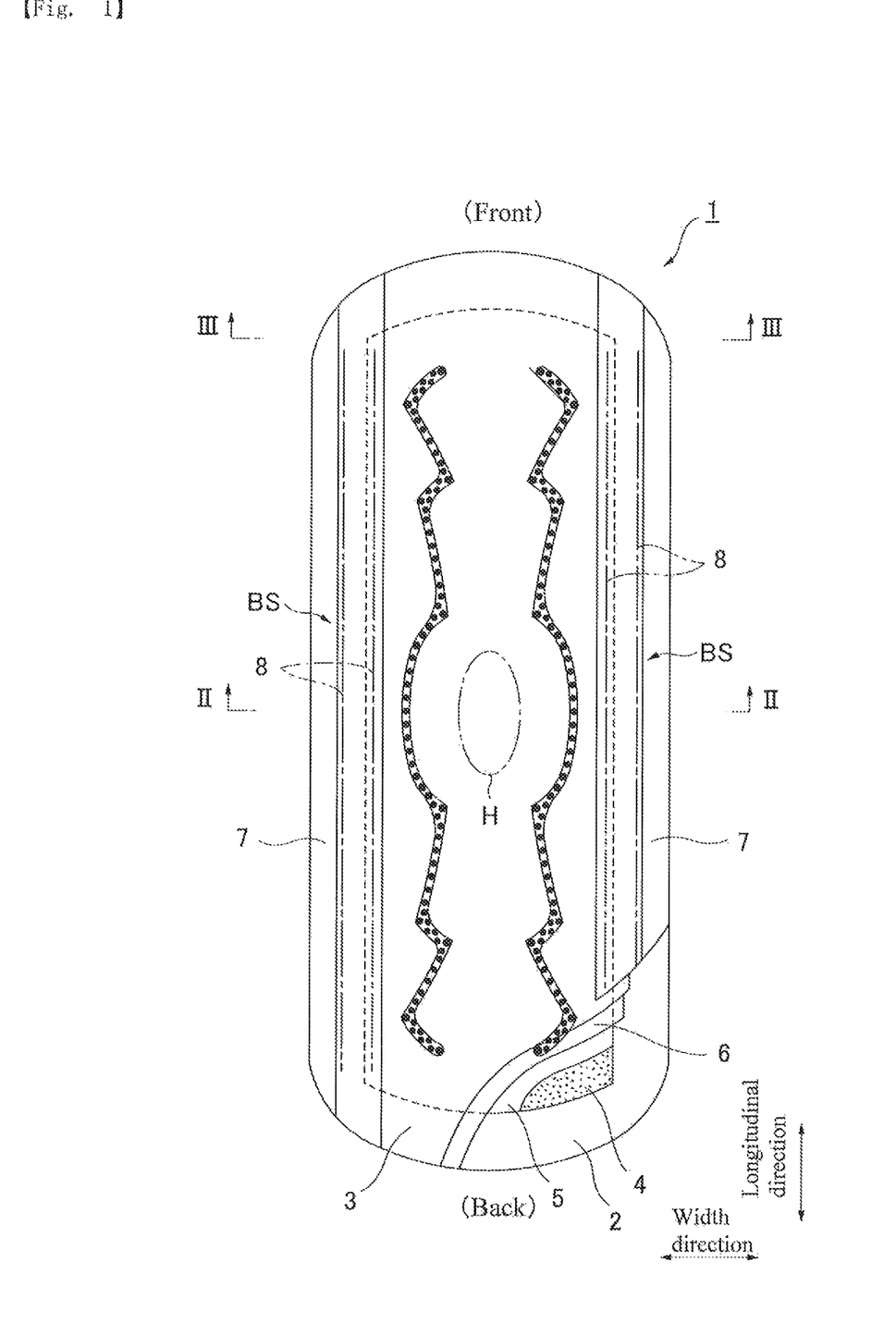
FIG. 1 Developed view, obtained by partially breaking, of an incontinence pad 1 according to the present invention.
Figure 2:
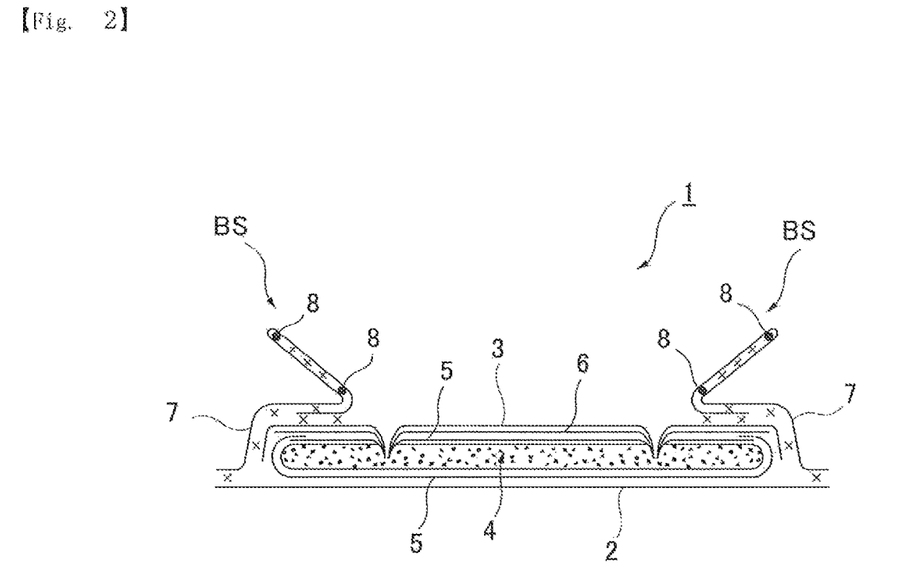
FIG. 2 Figure viewed from the arrow direction of II-II line of FIG. 1.
Figure 3:
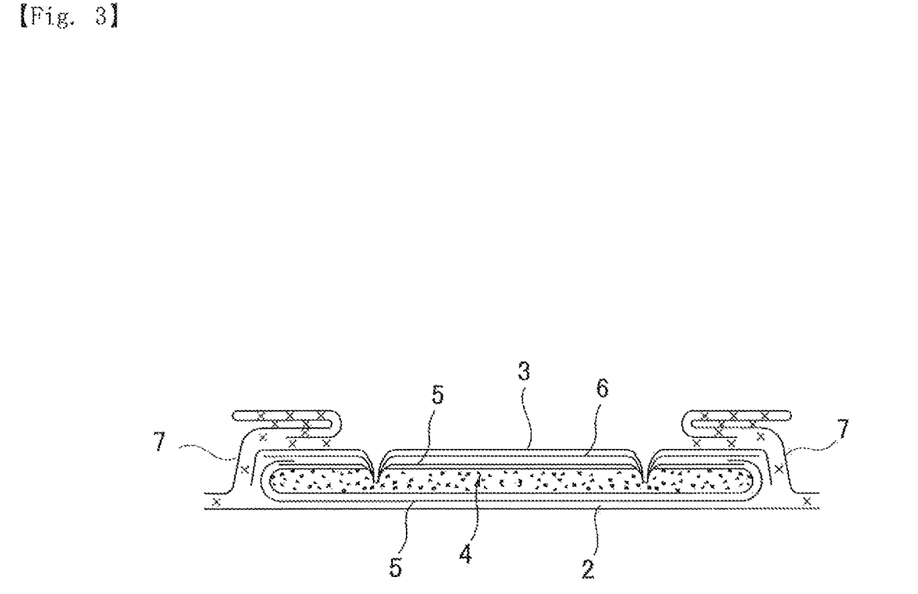
FIG. 3 Figure viewed from the arrow direction of III-III line of FIG. 1.

The incontinence pad 1 according to the present invention, as shown in FIG. 1 to FIG. 3, is primarily composed of a liquid-impermeable back-surface sheet 2, which is composed of e.g., a polyethylene sheet; a front-surface sheet 3, which forms a skin-contacting face and is configured to cause e.g., urine to quickly pass therethrough; an absorber 4, which is interposed between these sheets 2 and 3 and is composed of e.g., cotton pulp or synthetic pulp; and a pair of three-dimensional gathers BS, BS, one on the right and the other on the left, whose standing bases are at the substantially lateral edges of the absorber 4 and which are disposed to protrude toward the skin side within a predetermined region in the front/back direction at least so as to include a hole H for receiving urination from a wearer. The absorber 4 has such a periphery as follows: in the upper and lower edges of the absorber, the outer edge of the liquid-impermeable back-surface sheet 2 is bonded to the outer edge of the front-surface sheet 3 by using an adhesive such as a hot melt or by bonding means such as heat sealing; and in edges on both lateral sides of the absorber, the liquid-impermeable back-surface sheet 2, which laterally extends beyond the absorber 4, is bonded to a lateral-side nonwoven fabric 7, which forms the three-dimensional gather BS, by using an adhesive such as a hot melt or by bonding means such as heat sealing. The absorber 4, which is shown as a single-layer structure in the exemplary figures, may be a multi-layer structure that includes a central higher portion, or may be a multi-layer structure formed by stacking absorbers with the same size and shape.

The liquid-impermeable back-surface sheet 2 is formed of a sheet material at least having water-shielding property, such as polyethylene. The recent tendency is the use of sheets with properties including moisture permeability aimed at preventing stuffiness. The water-shielding and moisture-permeable sheet material is preferably a microporous sheet obtained by melt-kneading an olefin resin, such as polyethylene and polypropylene, having an inorganic filler therein, to form a sheet and thereafter stretching the sheet monoaxially or biaxially. The non-use side (external face) of the liquid-impermeable back-surface sheet 2 has one or more adhesive layers (not shown in the drawings); and the adhesive layers serve as fastening the incontinence pad 1 to underwear at the time of fitting to the body. The liquid-impermeable back-surface sheet 2 may be a polymer-laminated nonwoven fabric formed by laminating a plastic film and a nonwoven fabric on one another.

In the exemplary drawings, the front-surface sheet 3 has a somewhat larger width than a width of the absorber 4 and thereby covers the absorber 4, while the outward portion in the width direction of the front-surface sheet 3 is covered with the lateral-side nonwoven fabric 7 (a component different from the front-surface sheet 3) extending from both lateral side surfaces of the front-surface sheet 3. The center portion in the width direction of the lateral-side nonwoven fabric 7 forms the three-dimensional gather BS. The lateral-side nonwoven fabric 7 may be formed of a nonwoven fabric material having undergone water repellency treatment or hydrophilizing treatment as needed in accordance with purposes such as the prevention of e.g., urine from permeating and the enhancement of the texture felt to the skin. The lateral-side nonwoven fabric 7 may be formed from materials, such as natural fibers, synthetic fibers and regenerated fibers, that have undergone processing by appropriate means. For the purpose of removing the sense of stiffness and preventing the stuffiness, the use of nonwoven fabrics with their basis weight kept low and imparted with breathability is preferred. Specifically, the use of nonwoven fabrics produced so as to have a basis weight of 15 to 23 $g/m^2$ is preferred. For the purpose of ensuring the prevention of the body fluid permeation, the nonwoven fabrics are preferably subjected to water repellency treatment involving the coating with a water repellent agent, such as a silicon-based water repellent agent or a paraffin-based water repellent agent.

The lateral-side nonwoven fabric 7, as shown in FIG. 2 and FIG. 3, includes a portion bonded with an adhesive, such as a hot melt, which stretches outward from the middle portion in the width direction and which ranges from the inner position of the absorber 4, over a position somewhat beyond the lateral edge of the absorber, to the outer edge of the liquid-impermeable back-surface sheet 2.

The inward portion of the lateral-side nonwoven fabric 7 is to be substantially folded on itself to form a folding sheet. The inside of the folding sheet has, at its middle portion in its height direction, one or more filamentous elastic stretchable components that have fixed both ends or longitudinal portions determined as needed; in the exemplary drawings, two filamentous elastic stretchable components 8, 8 are disposed, having fixed both ends or longitudinal portions determined as needed. The folding sheet portions positioned at the front/back ends are folded on themselves and fixed to the front-surface sheet 3 side, as shown in FIG. 3.

<Front-Surface Sheet>

The front-surface sheet 3, which covers the skin side of the absorber 4 and forms the skin-contacting face, is characterized by being formed of a spunlace nonwoven fabric composed of 100 wt % of cotton fibers. Advantages of the spunlace nonwoven fabrics include the non-use of adhesives and their softness.

The nonwoven fabric of the front-surface sheet 3 is composed of cotton fibers alone and contains no synthetic fibers. Examples of the cotton fibers that may be used include various kinds of cotton fibers, such as raw cotton; cotton fibers refined and bleached; cotton fibers refined, bleached and thereafter dyed; defatted cotton fibers refined and bleached; and rag openings obtained by defibrating materials that form threads or fabrics. In particular, preferred are non-defatted cottons, which due to natural oil and fat of cotton wax adhering onto the cotton fibers have some degree of water repellency even at a fiber state.

The front-surface sheet 3 has a basis weight of 20 to 40 g/m², preferably 27 to 34 g/m², and more preferably 29 to 32 g/m²; and has a thickness of 0.25 to 0.50 mm, and preferably 0.3 to 0.4 mm. The basis weight is calculated by measuring ten sheets each 5 cm×30 cm with an electronic balance and converting the resultant values to values expressed in terms of square meter. The thickness is determined in accordance with JIS-L1906.

Figure 4:
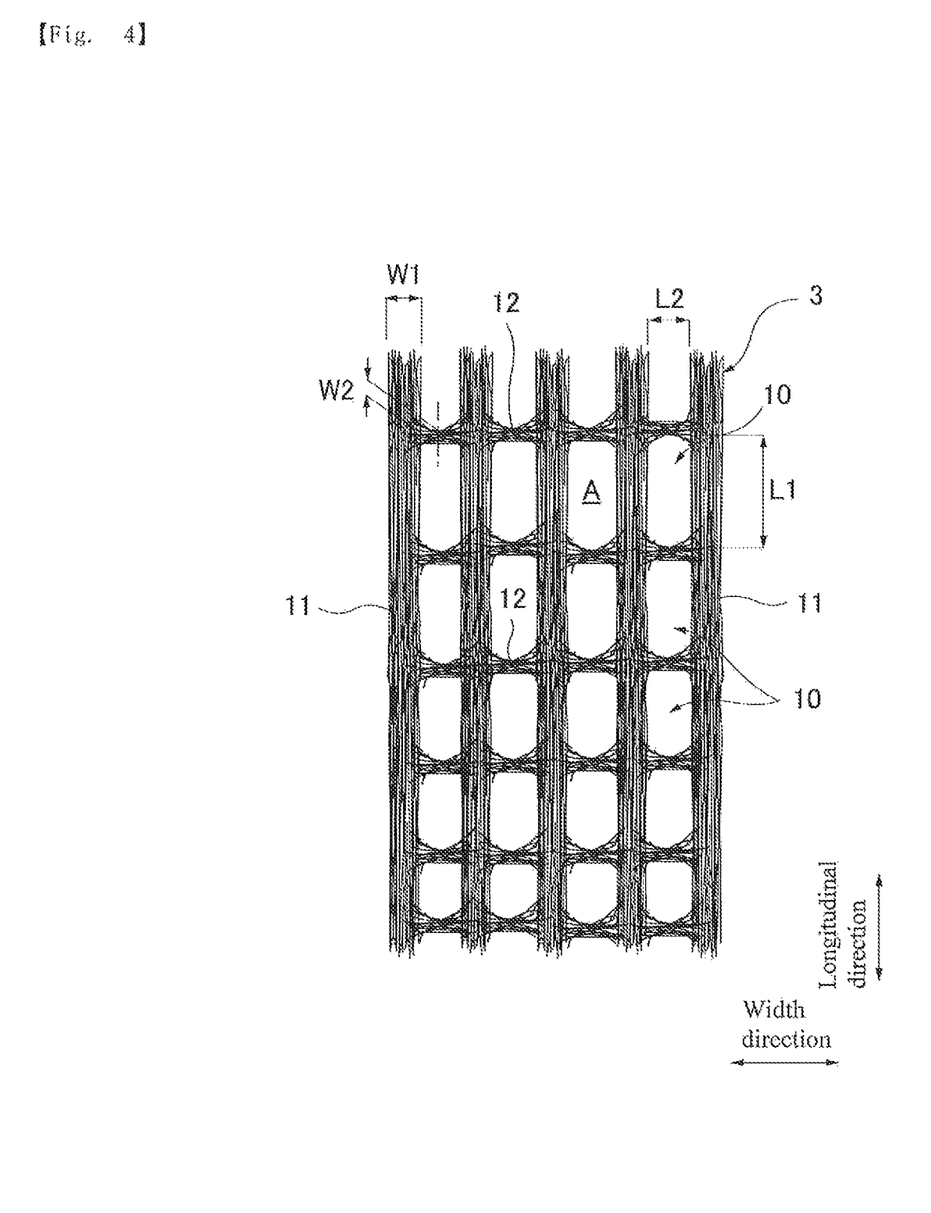
FIG. 4 Enlarged top view of a front-surface sheet 3.

To have an enhanced liquid-permeability, the front-surface sheet 3, as shown in FIG. 4, has numerous front-face/back-face penetrating openings 10, 10 . . . . Specifically, the formation of the openings 10 is made possible by allowing a fiber material to be carried by a mesh-like support in water-jet interlacing process at the time of spunlace production. At this time, changing requirements of the mesh material can regulate the size of the individual openings and opening rate. Needless to say, the formation of the openings may be done by punch-processing (punching) the resultant nonwoven fabrics. The openings 10, which may be provided across the whole of the front-surface sheet, are necessarily provided at least so as to include a portion H corresponding to an excreting hole. The openings are provided at a region that includes the portion H corresponding to an excreting hole and preferably represents 15% or more of a length of the absorber in the longitudinal direction of the product and 50% or more of a width of the absorber in the width direction of the product; and the openings are provided at a region that includes the portion H corresponding to an excreting hole and more preferably represents 50% or more of a length of the absorber in the longitudinal direction of the product and 70% or more of a width of the absorber in the width direction of the product. The opening-having region that represents less than 15% of a length of the absorber in the longitudinal direction of the product and less than 50% of a width of the absorber in the width direction of the product would be unable to cover an incontinence area, which would lead to the likelihood of the urine to remain on the front-surface sheet 3 thereby giving a feel of stickiness and causing skin problems such as itch and rash experienced at the time of fitting.

The front-surface sheet 3 is formed of the spunlace nonwoven fabric composed of 100 wt % of cotton fibers that is coated with a water repellent agent, and has numerous front-face/back-face penetrating openings at least at the portion corresponding to an excreting hole: this configuration gives a soft texture while realizing the inhibited occurrence of skin problems such as itch and rash even in long-hour wearing. The water repellent agent having been applied adequately addresses the problem of the liquid remaining on the front-surface. The configuration in which the front-surface sheet 3 has the front-face/back-face penetrating openings at least at its portion corresponding to an excreting hole allows the body fluid to promptly penetrate the front-surface sheet through those openings.

As shown in FIG. 4, the openings 10 are longer shaped in the longitudinal direction of the incontinence pad 1. Compared with circular-shaped openings, the openings shaped in that way allow the liquid to pass therethrough more easily, and through such openings 10, urine is able to pass through the front-surface sheet 3 more easily, resulting in the front-surface sheet 3 having a reduced water retention. In addition, the openings 10 allow urine passing therethrough to deform so as to have a longitudinally-longer shape; this configuration makes it possible to control the direction of urine diffusion to accord with the longitudinal direction of the pad thereby inhibiting transverse urine diffusion that would possibly cause sideward urine leakage. Those openings 10, unifying the shape of which is difficult in the case of spunlace though, include shapes that vary between generally-rectangular shapes and shapes of long-hole having a rounded corner, or that may be ellipse-like shapes.

Preferred dimensions of the openings 10 are as follows: a length in the longitudinal direction of the incontinence pad 1, L1, is 1.0 to 4.0 mm, and preferably 1.5 to 3.0 mm; and a length in the width direction of the incontinence pad 1, L2, is 0.5 to 1.5 mm, and preferably 0.5 to 1.0 mm. The openings 10 with a dimension of less than 0.5 mm would be accompanied by the difficulty in the passage of urine as well as in the formation of clearly-delimited openings due to the fuzz of the fibers. The openings 10 with a maximum dimension of more than 4.0 mm could cause the liquid to revert from the openings 10 and lead to the surface-exposure of the components of the absorber 4. The ratio of L1 to L2, i.e., L1/L2, is desirably 1.2 to 5.0, and preferably 2.0 to 3.0. The area A of the openings 10 is desirably 0.9 to 3.0 mm², and preferably 0.9 to 2.5 mm². The opening rate is desirably 15 to 45%, preferably 17 to 30%, and more preferably 18 to 25%. The openings 10, which have a dimension permitted not to be uniform across its entirety, may have any size within the above-mentioned ranges.

The front-surface sheet 3, as shown in FIG. 4, has a structure in which the cotton fibers form numerous longitudinal streaks 11, 11 . . . and numerous lateral streaks 12, 12 . . . wherein the longitudinal streaks extend along the longitudinal direction of the incontinence pad 1 and are formed with an interval in the width direction of the incontinence pad, and the lateral streaks extend along the width direction of the incontinence pad 1 and connect together the adjacent longitudinal streaks 11, 11 formed with an interval in the longitudinal direction of the incontinence pad; and the openings 10 are formed within portions surrounded by the longitudinal streaks 11 and the lateral streaks 12.

The width of the longitudinal streaks 11, W1, is desirably 0.5 to 2.5 mm, and preferably 0.8 to 2.3 mm. The width of the lateral streaks 12, W2, is desirably 0.2 to 1.6 mm, preferably 0.3 to 1.4 mm. The ratio of the width W1 to W2, i.e., W1/W2, is 1.2 to 2.0, and preferably 1.5 to 2.0. Designing the longitudinal streaks 11 so as to have a larger width W1 than the width W2 of the lateral streak 12 results in the easier liquid diffusion along the longitudinal streaks 11 in the longitudinal direction of the incontinence pad 1.

The longitudinal streaks 11 have more fibers and are formed at a higher density than the lateral streaks 12. This configuration allows the longitudinal streaks 11 alone to contact the skin, which reduces the skin contact area thereby leading to the inhibited occurrence of skin problems such as itch and rash even in long-hour wearing as well as alleviating the sense of stickiness even after incontinence. In passing through the front-surface sheet 3, urine is caused more easily to diffuse, along the relatively highly-dense longitudinal streaks 11, in the longitudinal direction of the incontinence pad 1, due to the capillary phenomenon exhibited by the fibers. Further, the diffusion direction of urine passing through the openings 10 accords with the diffusion direction of urine permeating the front-surface sheet 3 in the longitudinal direction of the incontinence pad 1. Under such configurations as described above, urine permeates the longitudinal streaks 11 of the front-surface sheet 3 in such a manner as is drawn by urine passing through the openings 10. Consequently, the liquid to remain on the front-surface sheet 3 is minimized.

The amount of the fibers can be measured in accordance with JIS P8207 "Pulps-Test method for classification with screens". The density can be measured in accordance with JIS P8118 "Test method for thickness and density".

The front-surface sheet 3 is externally coated with a water repellent agent. The water repellent agent to be used is selected, as needed, from known agents such as paraffin-based ones and silicon-based ones, and the selected agent must be the one that less stimulate the skin. As needed, it is more preferred to select fat and oil that less stimulate the skin: for example, glyceryl stearate, stearic acid amide, zinc stearate, calcium stearate, stearic acid diethanol amide, or magnesium stearate. Particularly preferred is glyceryl stearate. In using the water repellent agent composed of glyceryl stearate in the incontinence pad 1, its application amount is preferably 0.05 to 0.30 parts by weight with respect to 100 parts by weight of the fibers (in the case of the coating of both the faces of the front-surface sheet, the application amount defined here refers to the total amount applied onto both those faces). The application amount is more preferably 0.08 to 0.25 parts by weight. The application of the water repellent agent in an amount less than 0.05 parts by weight would sometimes lead to deficiency in water repellent effect. The application in an amount more than 0.30 parts by weight would lead to excessive water repellency, which contrarily would lead to the difficulty in water permeation.

The water repellent agent may be applied only on the skin-contacting face or may be applied on both the skin-contacting face and the face closer to the absorber 4. The water repellent agent is preferably applied such that the front-surface sheet at least has a water absorption amount, as determined in a water absorption amount test described later, of not more than 0.03 g, and preferably not more than 0.02 g.

The water absorption amount of the front-surface sheet 3 is determined by a procedure taken as follows in this order: (1) a 10 cm-square sample is prepared and its weight (A) is measured; (2) three pieces of 10 cm-square filter paper are stacked with their smooth surfaces facing upward, and thereon the sample is set; (3) on the set sample, 3 ml of tap water at ordinary temperature is dropped, and the sample is left to stand for 5 minutes; (4) a weight (B) of the sample left to stand for 5 minutes is measured; and (5) in view of (B)−(A)=water absorption amount (g), a water absorption amount (water retention amount) of the front-surface sheet 3 is determined.

Particularly, in a more preferred embodiment, the face closer to the absorber 4 of the front-surface sheet 3 has a water absorbing capacity that is higher than a water absorbing capacity of the skin-contacting face of the front-surface sheet 3. Thus, the water absorbing capacity (JIS L1907 Byreck method) of the skin-contacting face is 0 mm to 5 mm, and preferably 0 mm to 2 mm, while the water absorbing capacity (JIS L1907 Byreck method) of the face closer to the absorber 4 is 0 mm to 10 mm, and particularly preferably around 2 mm to 4 mm. Such a difference in water absorbing capacity is easily attainable by coating the skin-contacting face alone of the front-surface sheet 3 with the water repellent agent, and also by coating both faces of the front-surface sheet 3 with the water repellent agent in which case the face closer to the absorber 4 is coated with the agent in an amount less than an amount applied on the skin-contacting face. The application of the water repellent agent only on the skin-contacting face of the front-surface sheet 3 would sometimes cause the face closer to the absorber 4, too, to have water repellency, depending on the thickness and the basis weight. Whether the application of the water repellent agent will be done on the one face or both the faces and what the ratio in the application amount between both the faces will be in the case of the both-face coating are selected as needed, in view of requirements including the thickness, the basis weight and the openings of the front-surface sheet 3, so as to provide a good balance between liquid-permeability and hygroscopicity.

The water repellent agent may be applied in a known method such as transferring, spraying, brush coating, soaking or dipping, as needed. Creating the difference in the water absorbing capacity between both the faces of the sheet can be done favorably by transferring coating method.

Figure 5:
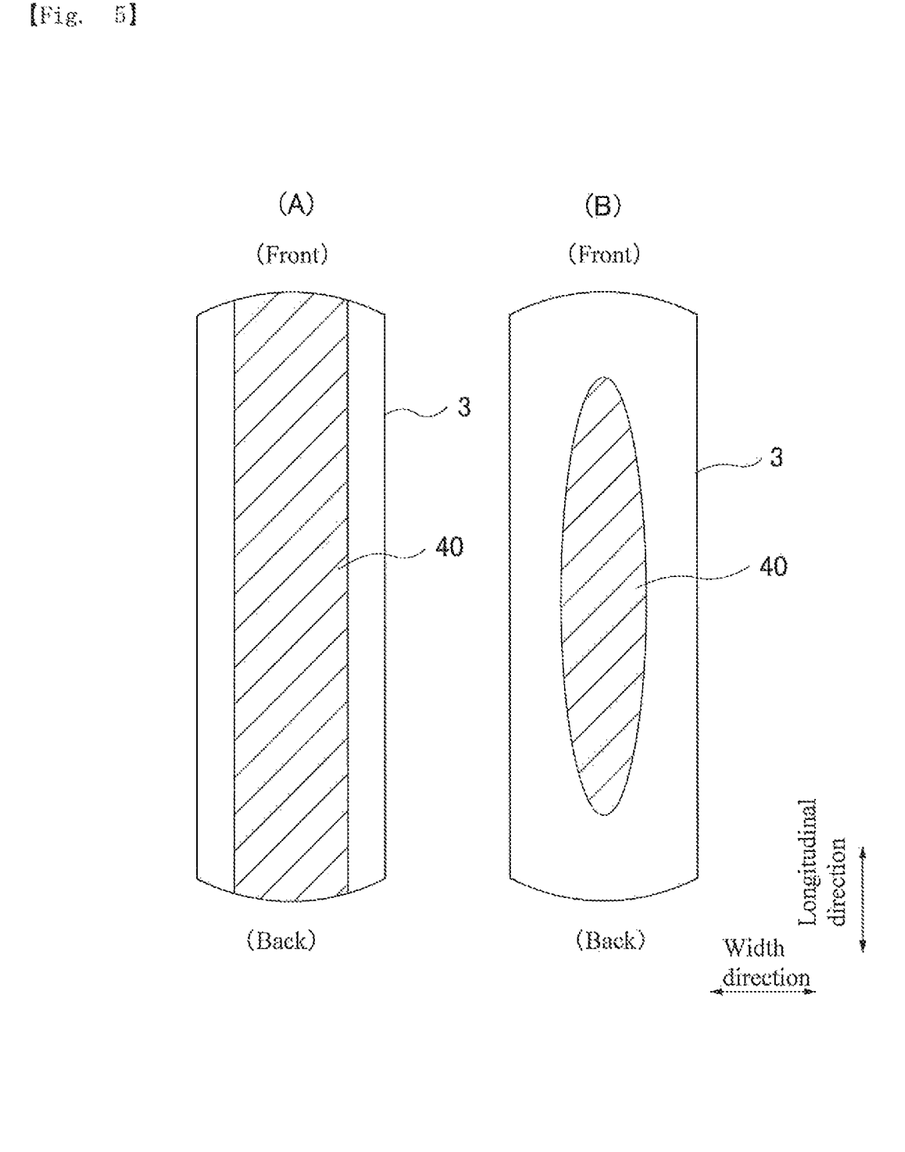
FIG. 5 Views of a developed surface of a front-surface sheet 3 on which a water repellent agent is applied, each view showing a pattern of the application of the agent.

The application of the water repellent agent is done preferably with respect to an entirety of the face of the sheet in terms of production efficiency. Alternatively, the application of the water repellent agent may be done only with respect to a portion receiving excretion liquid of the face of the sheet: for instance, a water repellent agent-coated portion 40, which excludes both side portions in the width direction, may be provided as shown in FIG. 5(A); and as shown in FIG. 5(B), the water repellent agent-coated portion 40 may be located only at the center in the width direction and at the middle portion in the front/back direction.

<Absorber 4>

The absorber 4 is made of a material that is capable of absorbing and retaining urine and is given by incorporating and dispersing powdery superabsorbent polymers in fluffy pulp fibers. The absorber 4 consists of the pulp fibers and the superabsorbent polymers alone and contains no synthetic fibers.

Examples of the pulp fibers include cellulose fibers such as chemical pulps and dissolving pulps that are obtainable from wood, and artificial cellulose fibers such as rayon and acetate. Softwood pulps, whose fiber length is larger, are suitably used in terms of function and price, rather than hardwood pulps.

The pulp fibers desirably have a basis weight of 75 to 300 $g/m^2$, and preferably 155 to 270 $g/m^2$; and the superabsorbent polymers desirably have a basis weight of 85 to 185 $g/m^2$, and preferably 100 to 165 $g/m^2$.

Examples of the superabsorbent polymers include polyacrylate salt crosslinked products, self-crosslinked polyacrylate salts, saponification products of acrylic acid ester/vinyl acetate copolymer crosslinked products, isobutylene/maleic anhydride copolymer crosslinked products, polysulfonate salt crosslinked products, and partially-crosslinked products of water-swelling polymers such as polyethylene oxide and polyacrylamide. Preferred among these are acrylic acid-based ones and acrylate salt-based ones, which excel in water absorption amount and water absorption speed. Those superabsorbent polymers with water absorption capacity can have controlled absorption ratio (absorptive ability) and absorption speed by regulating their crosslinking density and their crosslinking density gradient during the production process.

The ratio of the pulp fibers to the superabsorbent polymers is desirably as follows: pulp fibers:superabsorbent polymers=70-30 wt %: 30-70 wt %, preferably 62-45 wt %: 38-55 wt %, and more preferably 60-50 wt %: 40-50 wt %.

In the incontinence pad 1 according to the present invention, the absorber is composed of the pulp fibers and the superabsorbent polymers, each component at the specific basis weight, at the specific weight ratio of the pulp fibers to the superabsorbent polymers. Urine even if instantaneously excreted would be quickly absorbed, immediately after urination, by the pulp fibers, which have a higher absorption speed, and thereafter the urine absorbed by the pulp fibers is gradually absorbed and retained by the superabsorbent polymers, whereby urine is completely prevented from reverting to the front-surface.

The incorporation of the pulp fibers at more than 70 wt % and the superabsorbent polymers at less than 30 wt %, which means a higher content ratio of the pulp fibers, would reduce the liquid retainability of the absorber 4, which leads to the likeliness of the urine to revert to the front-surface sheet 3 after urination. The incorporation of the pulp fibers at less than 30 wt % and the superabsorbent polymers at more than 70 wt %, which means a higher content ratio of the superabsorbent polymers, would reduce the initial absorption speed immediately after the urination, which inhibits the smooth migration of urine from the front-surface sheet 3 to the absorber 4 thereby leading to the likeliness of the urine to remain on the front-surface sheet 3 immediately after urination.

The configuration defined above of the present invention ensures that urine is absorbed and retained within the absorber immediately after urination without remaining on the front-surface sheet, and therefore can inhibit the urine diffusion range from spreading on the front-surface sheet.

The absorber 4 is desirably enclosed by a wrapping sheet 5, such as crepe paper, for purposes such as the shape retention and polymer powder retention.

<Intermediate Sheet>

The front-surface sheet 3, included in the incontinence pad 1 according to the present invention, has the numerous openings 10. To prevent the exposure, from the openings 10, of the pulps, polymers, adhesives and others that constitute the absorber 4, it is preferred that between the front-surface sheet 3 and the absorber 4, an intermediate sheet 6 is disposed. The intermediate sheet 6 provides other benefits such as the prevention of the liquid from reverting from the absorber 4 and cushioning effect giving a soft texture to those wearing the product.

The intermediate sheet 6, which is shown as a single-layer structure in exemplary drawings, may be folded in a tubular manner to form a two-layer structure. The intermediate sheet 6 may be provided across an entirety of the skin-contacting face or may be provided only at the center in the width direction and at the middle part in the front/back direction (particularly, crotch part).

Any materials that have liquid permeability may be used as the intermediate sheet 6, and particularly preferred are those having hydrophilicity. Combining such a hydrophilic intermediate sheet 6 with the water-repellent front-surface sheet 3 equipped with the openings of the present invention enables the front-surface sheet 3 to attain outstanding enhancement in liquid permeability and the liquid reversion preventability. Examples of such materials with hydrophilicity that may be used include regenerated fibers, such as rayon and cupra, and natural fibers, such as cotton, i.e., the use of hydrophilic materials; and synthetic fibers including fibers of olefins, such as polyethylene and polypropylene, polyester fibers, polyamide fibers, and composite fibers, copolymers and blends thereof, which are to be used after surface-treated with a hydrophilizing agent to be given hydrophilicity. Preferred is the use of mixed fibers of polyethylene and polypropylene. The fibers constituting the nonwoven fabric may be any of long fibers, short fibers and combinations of these fibers. The fineness is around 3.0 to 7.0 dtex, and preferably around 4 to 6 dtex. The intermediate sheet 6 may be formed of known mobile nonwoven fabrics such as air-through, air laid, spunbond and other nonwoven fabrics, but preferred is air-through nonwoven fabric, which does not lower the breathability.

There are many cases where incontinence pads keep being used until incontinence experienced for the second time, as described above. In view of this, it is more preferred, rather than merely relying on hydrophilic nonwoven fabrics, to use strong-hydrophilic or durable-hydrophilic nonwoven fabrics given by spraying the nonwoven fabrics with a strong-hydrophilic and/or durable-hydrophilic agent. The nonwoven fabric sprayed with a strong-hydrophilic or durable-hydrophilic agent desirably has a basis weight of 10 to 40 g/m$^2$, and preferably around 25 g/m$^2$. The intermediate sheet 6 preferably has a basis weight of 20 to 30 g/m$^2$.

To prevent urine liquid remaining and to inhibit the occurrence of skin problems such as itch and rash experienced at the time of fitting, in a preferable embodiment, the front-surface sheet 3 has the numerous front-face/back-face penetrating openings 10 at its region that includes the portion H corresponding to an excreting hole and represents 15% or more of a length of the absorber in the product length direction and 50% or more of a width of the absorber in the product width direction. In view of this configuration, the intermediate sheet 6 is disposed at least with such a size as to cover an entirety of such an opening-having region. Specifically, it is preferred that the size at 9% or more of the size of the absorber 4 covers an entirety of the opening-having region.

The bonding of the intermediate sheet to the front-surface sheet 3, which cannot be done by heat embossing, is desirably done with a hot melt adhesive. The hot melt adhesive, the type of which is not limited though, is particularly preferably a SBS (styrene-butadiene-styrene block copolymer)-based hot melt adhesive.

EXAMPLE

[Test 1]

The invention provides an incontinence pad with a front-surface sheet that is formed of a spunlace nonwoven fabric composed of cotton fibers 100% having undergone a water repellent treatment and that has numerous openings. Effects resulting from those configurations of the present invention were functionally evaluated to demonstrate those effects. The evaluation consisted of two kinds of evaluations: labo-evaluation (laboratory evaluation) and actual-use evaluation. Labo-evaluation: 10 cc of urine was poured in the vicinity of a portion receiving urination, and five minutes thereafter, the front-surface of the absorbent article was touched by hands and evaluated with three grades: Good: ○, Mediocre: Δ, Poor: x. Actual-use evaluation: products were worn by 20 female testers, who evaluated those products with three grades: Good: ○, Mediocre: Δ, Poor: x.

The test employed an incontinence pad with a basic structure including a front-surface sheet that was opening-having nonwoven fabric that was formed of non-defatted or defatted cotton fibers 100 wt % (basis weight: 30 g/m$^2$, thickness: 0.35 mm) and that was coated with a water repellent agent, and including an absorber composed of pulp fibers with a basis weight of 155 g/m$^2$ and superabsorbent polymers with a basis weight of 145 g/m$^2$ at a ratio of pulp fibers:superabsorbent polymers=51 wt %: 49 wt %, in Examples 1 and 2. These examples were compared with Comparative Example 1, where the cotton fibers were defatted, no water repellency treatment was done, and the openings were formed; Comparative Example 2, where the cotton fibers were defatted, no water repellency treatment was done, and no openings were formed; Comparative Example 3, where the cotton fibers were non-defatted, the water repellency treatment was done, and no openings were formed; and Comparative Example 4, where the cotton fibers were defatted, the water repellency treatment was done, and no openings were formed.

The same second sheet (intermediate sheet): PE/PP 5.6 dtex, air-through nonwoven fabric 25 g/m$^2$ (durable-hydrophilic) was used.

Results of the test are shown in Table 1.

TABLE 1

| Item | Example 1 | Example 2 | Comparative Example 1 | Comparative Example 2 | Comparative Example 3 | Comparative Example 4 |
|---|---|---|---|---|---|---|
| Water repellency treatment | done | done | undone | undone | done | done |
| Presence/Absence of Openings | present | present | present | absent | absent | absent |
| Defatted or Non-defatted (Labo-evaluation) | non-defatted | defatted | defatted | defatted | non-defatted | defatted |
| Dry touch felt after absorption (Actual-use evaluation) | ○ | ○ | X | X | X | X |
| Dry touch of front-surface sheet felt before urination | ○ | ○ | ○ | ○ | ○ | ○ |
| Dry tough felt immediately after urination | ○ | ○ | X | X | X | X |
| Dry tough felt with passage of time after urination | ○ | ○ | X | X | X | X |

[Test 2]

In Test 2, individual front-surface sheets varying in terms of an area per one opening, opening dimension ratio, opening-having region (length·width), and opening rate (%) were functionally evaluated to demonstrate the effects. The evaluation consisted of two kinds of evaluations: labo-evaluation (laboratory evaluation) and actual-use evaluation. Labo-evaluation: 10 cc of urine was poured in the vicinity of a portion receiving urination, and five minutes thereafter, the front-surface of the absorbent article was touched by hands and evaluated with four grades: Very Good: ◎, Good: ○, Mediocre: Δ, Poor: x. Actual-use evaluation: products were worn by 20 female testers, who evaluated those products with four grades: Very Good: ◎, Good: ○, Mediocre: Δ, Poor: x.

The test employed an incontinence pad with a basic structure including a front-surface sheet that was opening-having nonwoven fabric composed of non-defatted cotton fibers 100 wt % (basis weight: 30 g/m², thickness: 0.35 mm), and that was coated with a water repellent agent, and including an absorber composed of pulp fibers with a basis weight of 155 g/m² and superabsorbent polymers with a basis weight of 145 g/m² at a ratio of pulp fibers:superabsorbent polymers=51 wt %: 49 wt %, the absorber having a length of 170 mm and a width of 65 mm, in Examples 3 to 22.

The same second sheet (intermediate sheet): PE/PP 5.6 dtex, air-through nonwoven fabric 25 g/m² (durable-hydrophilic) was used with a varying size in the test.

Results of the test are shown in Table 2.

TABLE 2

| | Item | Example 3 | Example 4 | Example 5 | Example 6 | Example 7 | Example 8 | Example 9 |
|---|---|---|---|---|---|---|---|---|
| | Length of product (mm) | 210 | 210 | 210 | 210 | 210 | 210 | 210 |
| | Width of product (mm) | 90 | 90 | 90 | 90 | 90 | 90 | 90 |
| | Length of absorber (mm) | 170 | 170 | 170 | 170 | 170 | 170 | 170 |
| | Width of absorber (mm) | 65 | 65 | 65 | 65 | 65 | 65 | 65 |
| Properties of openings | Area per one opening (mm²) | 2.2 | 2.2 | 2.2 | 2.2 | 2.2 | 1.0 | 1.0 |
| | Opening dimension ratio (length · width) | 2.0 | 2.0 | 2.0 | 2.0 | 2.0 | 1.6 | 1.6 |
| | Dimension of opening-having region in length direction of product (mm) | 170 | 170 | 170 | 170 | 170 | 170 | 170 |
| | Ratio of opening-having region to length of absorber (the region includes urination hole and is in length direction of product) (%) | 100 | 100 | 100 | 100 | 100 | 100 | 100 |
| | Dimension of opening-having region in width direction of product (mm) | 65 | 65 | 65 | 65 | 65 | 65 | 65 |
| | Ratio of opening-having region to width of absorber (the region includes urination hole and is in width direction) (%) | 100 | 100 | 100 | 100 | 100 | 100 | 100 |
| | Opening rate*¹ | 15 | 22 | 45 | 10 | 50 | 15 | 45 |
| Intermediate sheet | Length of intermediate sheet in direction of product (mm) | 170 | 170 | 170 | 170 | 170 | 170 | 170 |
| | Length of intermediate sheet in width direction of product (mm) | 65 | 65 | 65 | 65 | 65 | 65 | 65 |
| | Size of intermediate sheet*² (Labo-evaluation) | 100 | 100 | 100 | 100 | 100 | 100 | 100 |
| | Dry touch felt after absorption (Actual-use evaluation) | ◎ | ◎ | ◎ | ○ | ○ | ◎ | ◎ |
| | Dry touch of front-surface sheet felt before urination | ◎ | ◎ | ◎ | ◎ | ◎ | ◎ | ◎ |

TABLE 2-continued

| | | | | | | | |
|---|---|---|---|---|---|---|---|
| Dry tough felt immediately after urination | ◎ | ◎ | ◎ | ○ | ○ | ◎ | ◎ |
| Dry tough felt with passage of time after urination | ◎ | ◎ | ◎ | ○ | ○ | ◎ | ◎ |

*¹Opening rate: proportion (%) of total area of openings relative to total area of opening-having region
*²Size of intermediate sheet: proportion (%) of size of intermediate sheet relative to area of absorber under the condition that the intermediate sheet covers the entire surface of the opening-having region

| | Item | Example 10 | Example 11 | Example 12 | Example 13 | Example 14 | Example 15 | Example 16 |
|---|---|---|---|---|---|---|---|---|
| | Length of product (mm) | 210 | 210 | 210 | 210 | 210 | 210 | 210 |
| | Width of product (mm) | 90 | 90 | 90 | 90 | 90 | 90 | 90 |
| | Length of absorber (mm) | 170 | 170 | 170 | 170 | 170 | 170 | 170 |
| | Width of absorber (mm) | 65 | 65 | 65 | 65 | 65 | 65 | 65 |
| Properties of openings | Area per one opening (mm²) | 3.0 | 3.0 | 0.5 | 0.5 | 0.5 | 4.0 | 4.0 |
| | Opening dimension ratio (length · width) | 1.6 | 1.6 | 1.2 | 1.2 | 1.2 | 2.0 | 2.0 |
| | Dimension of opening-having region in length direction of product (mm) | 170 | 170 | 170 | 120 | 120 | 170 | 120 |
| | Ratio of opening-having region to length of absorber (the region includes urination hole and is in length direction of product) (%) | 100 | 100 | 100 | 71 | 71 | 100 | 71 |
| | Dimension of opening-having region in width direction of product (mm) | 65 | 65 | 65 | 52 | 52 | 65 | 52 |
| | Ratio of opening-having region to width of absorber (the region includes urination hole and is in width direction) (%) | 100 | 100 | 100 | 80 | 80 | 100 | 80 |
| | Opening rate*¹ | 15 | 45 | 15 | 45 | 45 | 15 | 45 |
| Intermediate sheet | Length of intermediate sheet in direction of product (mm) | 170 | 170 | 170 | 125 | 170 | 170 | 125 |
| | Length of intermediate sheet in width direction of product (mm) | 65 | 65 | 65 | 57 | 65 | 65 | 57 |
| | Size of intermediate sheet*² | 100 | 100 | 100 | 64 | 100 | 100 | 64 |
| | (Labo-evaluation) | | | | | | | |
| | Dry touch felt after absorption (Actual-use evaluation) | ◎ | ◎ | ○ | ○ | ○ | ○ | ○ |
| | Dry touch of front-surface sheet felt before urination | ◎ | ◎ | ◎ | ◎ | ◎ | ◎ | ◎ |
| | Dry tough felt immediately after urination | ◎ | ◎ | ○ | ○ | ○ | ○ | ○ |
| | Dry tough felt with passage of time after urination | ◎ | ◎ | ○ | ○ | ○ | ○ | ○ |

*¹Opening rate: proportion (%) of total area of openings relative to total area of opening-having region
*²Size of intermediate sheet: proportion (%) of size of intermediate sheet relative to area of absorber when the intermediate sheet covers the entire surface of the opening-having region

| | Item | Example 17 | Example 18 | Example 19 | Example 20 | Example 21 | Example 22 |
|---|---|---|---|---|---|---|---|
| | Length of product (mm) | 210 | 210 | 210 | 210 | 210 | 210 |
| | Width of product (mm) | 90 | 90 | 90 | 90 | 90 | 90 |
| | Length of absorber (mm) | 170 | 170 | 170 | 170 | 170 | 170 |
| | Width of absorber (mm) | 65 | 65 | 65 | 65 | 65 | 65 |
| Properties of openings | Area per one opening (mm²) | 2.2 | 2.2 | 2.2 | 2.2 | 2.2 | 2.2 |
| | Opening dimension ratio (length · width) | 2.0 | 2.0 | 2.0 | 2.0 | 2.0 | 2.0 |
| | Dimension of opening-having region in length direction of product (mm) | 85 | 85 | 85 | 85 | 26 | 17 |
| | Ratio of opening-having region to length of absorber (the region includes urination hole and is in length direction of product) (%) | 50 | 50 | 50 | 50 | 15 | 10 |
| | Dimension of opening-having region in width direction of product (mm) | 46 | 46 | 46 | 46 | 33 | 30 |

TABLE 2-continued

| | | | | | | | |
|---|---|---|---|---|---|---|---|
| | Ratio of opening-having region to width of absorber (the region includes urination hole and is in width direction) (%) | 71 | 71 | 71 | 71 | 51 | 46 |
| | Opening rate*¹ | 15 | 22 | 22 | 45 | 15 | 15 |
| Intermediate sheet | Length of intermediate sheet in direction of product (mm) | 90 | 90 | 170 | 90 | 28 | 170 |
| | Length of intermediate sheet in width direction of product (mm) | 50 | 50 | 65 | 50 | 36 | 65 |
| | Size of intermediate sheet*² (Labo-evaluation) | 41 | 41 | 100 | 41 | 9 | 100 |
| Dry touch felt after absorption (Actual-use evaluation) | | ◎ | ◎ | ◎ | ◎ | ◎ | ○ |
| Dry touch of front-surface sheet felt before urination | | ◎ | ◎ | ◎ | ◎ | ◎ | ◎ |
| Dry tough felt immediately after urination | | ◎ | ◎ | ◎ | ◎ | ◎ | ○ |
| Dry tough felt with passage of time after urination | | ◎ | ◎ | ◎ | ◎ | ◎ | ○ |

*¹Opening rate: proportion (%) of total area of openings relative to total area of opening-having region
*²Size of intermediate sheet: proportion (%) of size of intermediate sheet relative to area of absorber when the intermediate sheet covers the entire surface of the opening-having region

REFERENCE SIGNS LIST

1: Incontinence pad
2: Liquid-impermeable back-surface sheet
3: Front-surface sheet
4: Absorber
5: Wrapping sheet
6: Intermediate sheet
7: Lateral-side nonwoven fabric
8: Filamentous elastic stretchable component
10: Openings
11: Longitudinal streaks
12: Lateral streaks

The invention claimed is:

1. An absorbent article comprising a front-surface sheet, a back-surface sheet, and an absorber interposed between the front-surface sheet and the back-surface sheet, wherein:
the absorbent article is an incontinence pad for use in absorbing urine at a medium or more volume that is 20 cc or more;
the front-surface sheet is formed of a spunlace nonwoven fabric 100 wt % of which is composed of cotton fibers and which is coated with a water repellent agent, and has, at least at a portion corresponding to an excreting hole, numerous front-face/back-face penetrating openings that are longer shaped in the longitudinal direction of the absorbent article; and
the cotton fibers form numerous longitudinal streaks and numerous lateral streaks, the longitudinal streaks extending along the longitudinal direction of the absorbent article and being formed with an interval in the width direction of the absorbent article, and the lateral streaks extending along the width direction of the absorbent article and connecting together the longitudinal streaks formed with an interval in the longitudinal direction of the absorbent article; the openings are formed within portions surrounded by the longitudinal streaks and the lateral streaks; and the longitudinal streaks have more fibers and are formed at a higher density than the lateral streaks.

2. The absorbent article according to claim 1, wherein the absorber is composed of synthetic fibers-free pulp fibers and superabsorbent polymers; the pulp fibers have a basis weight of 75 to 300 g/m² and the superabsorbent polymers have a basis weight of 85 to 185 g/m²; and a ratio of the pulp fibers to the superabsorbent polymers is pulp fibers: superabsorbent polymers=70-30 wt %: 30 to 70 wt %.

3. The absorbent article according to claim 2, wherein the front-surface sheet is formed of non-defatted cotton fibers.

4. The absorbent article according to claim 3, wherein the water repellent agent comprises glyceryl stearate.

5. The absorbent article according to claim 2, wherein the water repellent agent comprises glyceryl stearate.

6. The absorbent article according to claim 1, wherein the front-surface sheet is formed of non-defatted cotton fibers.

7. The absorbent article according to claim 6, wherein the water repellent agent comprises glyceryl stearate.

8. The absorbent article according to claim 1, wherein the water repellent agent comprises glyceryl stearate.

* * * * *